United States Patent [19]

Meirowitz et al.

[11] Patent Number: 5,342,336
[45] Date of Patent: Aug. 30, 1994

[54] ABSORBENT STRUCTURE FOR MASKING AND DISTRIBUTING A LIQUID

[75] Inventors: Randy E. Meirowitz, Neenah; Sriram P. Anjur; Robert J. Phelan, both of Appleton; Kim T. Tang, Neenah, all of Wis.

[73] Assignee: Kimberly-Clark Corporation, Neenah, Wis.

[21] Appl. No.: 852,848

[22] Filed: Mar. 16, 1992

Related U.S. Application Data

[63] Continuation-in-part of Ser. No. 810,259, Dec. 19, 1991, abandoned.

[51] Int. Cl.⁵ .................................................. A61F 13/15
[52] U.S. Cl. ..................................... 604/378; 604/358
[58] Field of Search ............... 604/358, 360, 367, 368, 604/378; 428/172, 212, 284, 286

[56] References Cited

U.S. PATENT DOCUMENTS

| | | | |
|---|---|---|---|
| Re. 31,380 | 9/1983 | Smith | 106/164 |
| 2,336,743 | 12/1943 | Manning | 18/8 |
| 2,945,739 | 7/1960 | Lehmicke | 18/54 |
| 3,169,899 | 2/1965 | Steuber | 161/72 |
| 3,276,944 | 10/1966 | Levy | 161/150 |
| 3,314,840 | 4/1967 | Lloyd et al. | 156/167 |
| 3,368,934 | 2/1968 | Vosburgh, Sr. | 161/150 |
| 3,509,009 | 4/1970 | Hartmann | 161/150 |
| 3,554,854 | 1/1971 | Hartmann | 161/150 |
| 3,630,816 | 12/1971 | Parker | 161/72 |
| 3,670,069 | 6/1972 | Mitchell et al. | 264/187 |
| 3,865,918 | 2/1975 | Mitchell et al. | 264/188 |
| 3,984,515 | 10/1976 | Mommaerts et al. | 264/182 |
| 4,129,679 | 12/1978 | Woodings | 428/398 |
| 4,144,079 | 3/1979 | Smith | 106/164 |
| 4,179,259 | 12/1979 | Belitsin et al. | 425/461 |
| 4,213,459 | 7/1980 | Sigl et al. | 128/287 |
| 4,360,022 | 11/1982 | Usami et al. | 128/290 R |
| 4,468,428 | 8/1984 | Early et al. | 428/221 |
| 4,469,746 | 9/1984 | Weisman et al. | 428/289 |
| 4,668,566 | 5/1987 | Braun | 428/286 |
| 4,699,619 | 10/1987 | Bernardin | 604/378 |
| 4,710,187 | 12/1987 | Boland et al. | 604/385 A |
| 4,753,834 | 6/1988 | Braun et al. | 428/74 |
| 4,762,521 | 8/1988 | Roessler et al. | 604/38 SA |
| 4,770,656 | 9/1988 | Proxmire et al. | 604/393 |
| 4,778,460 | 10/1988 | Braun et al. | 604/380 |
| 4,781,962 | 11/1988 | Zamarripa et al. | 428/172 |
| 4,783,231 | 11/1988 | Raley | 156/167 |
| 4,798,603 | 1/1989 | Meyer et al. | 604/378 |
| 4,885,202 | 12/1989 | Lloyd et al. | 428/172 |
| 4,944,735 | 7/1990 | Mokry | 604/385.2 |
| 5,006,057 | 4/1991 | Bagrodia et al. | 425/464 |
| 5,200,248 | 4/1993 | Thompson et al. | 428/131 |
| 5,281,208 | 1/1994 | Thompson et al. | 604/378 |

FOREIGN PATENT DOCUMENTS

| | | |
|---|---|---|
| 0301874A1 | 2/1989 | European Pat. Off. |
| 0391814A2 | 10/1990 | European Pat. Off. |
| 54-138617 | 10/1979 | Japan |
| 62-53605 | 11/1987 | Japan |
| 63-227871 | 9/1988 | Japan |
| WO91/12949 | 9/1991 | PCT Int'l Appl. |
| WO93/01779 | 2/1993 | PCT Int'l Appl. |
| WO93/01780 | 2/1993 | PCT Int'l Appl. |
| WO93/01781 | 2/1993 | PCT Int'l Appl. |
| WO93/01782 | 2/1993 | PCT Int'l Appl. |
| WO93/01783 | 2/1993 | PCT Int'l Appl. |
| WO93/01784 | 2/1993 | PCT Int'l Appl. |
| WO93/02235 | 2/1993 | PCT Int'l Appl. |
| 2085304A | 4/1982 | United Kingdom |
| 2215609A | 9/1989 | United Kingdom |

OTHER PUBLICATIONS

A Simplified Thermodynamic Approach to Capillarity–Journal of Colloid Science 14, pp. 572–583 (1959).
Spinnerettes–Nippon Nozzle Co., Ltd.–Moving Ahead . . . Spinnerettes, Inc.

*Primary Examiner*—Randall L. Green
*Assistant Examiner*—Rob Clarke
*Attorney, Agent, or Firm*—John R. Schenian; Thomas J. Mielke

[57] ABSTRACT

A structure for absorbing and transporting a liquid. The structure includes a masking layer having from 0 to about 90 weight percent shaped fibers and a distribution layer having from 100 to about 10 weight percent shaped fibers.

27 Claims, 3 Drawing Sheets

ABSORBENT STRUCTURE FOR MASKING AND DISTRIBUTING A LIQUID

This is a continuation-in-part of copending application Ser. No. 07/810,259 filed on Dec. 19, 1991 abandoned.

BACKGROUND OF THE INVENTION

1. Field of the Invention

The present invention relates to absorbent structures. Specifically, the present invention relates to an absorbent structure comprising a nonwoven masking layer and a nonwoven distribution layer.

2. Description of the Related Art

A variety of absorbent structures are known for use in disposable absorbent products intended to absorb body fluids. Examples of such products include diapers, feminine care products, training pants, adult incontinence products and the like. In general, one of the most economical, liquid-absorbent materials for use in such products is cellulosic fibers, such as comminuted wood pulp fluff. While being absorbent, undensified wood pulp fluff typically does not transport or distribute a liquid particularly well. Thus, liquid absorbed by undensified wood pulp fluff tends to remain in the fluff at the point where it is initially absorbed.

Various solutions have been proposed to allow wood pulp fluff to better distribute an absorbed liquid. For example, U.S. Pat. No. 4,213,459 to Sigl describes decreasing the pore size of an absorbent material along the length of an absorbent product. The improved capillary action of the pores overcomes the force of gravity and causes liquid to move along the length of the absorbent product. The reduction in pore size tends to reduce the total absorption capacity of the absorbent batt.

In an attempt to improve on the teachings of Sigl, U.S. Pat. No. 4,699,619, issued Oct. 13, 1987, to Bernardin, describes a two-layer structure for absorption of body fluids. The upper layer has a lower density and/or larger pore size than the lower layer. The upper layer serves as an acquisition layer to initially absorb a liquid at the point of liquid application. The absorbed liquid is then drawn into the lower layer, having a higher density or smaller pore size, and is transported throughout the lower layer so as to desorb the portion of the upper layer where liquid waste initially accumulated. After the lower layer distributes the absorbed liquid, the liquid is free to transfer from the lower layer back into the upper layer at points remote from the location of initial fluid insult. While such a two-layer approach has proven effective, densification of the lower layer tends to reduce the absorbent capacity of the lower layer.

The use of shaped fibers to form various woven and nonwoven products is known. For example, U.S. Pat. No. 4,129,679 issued Dec. 12, 1978, to Woodings describes regenerated cellulose filaments having a collapsed hollow structure and a multi-limbed cross section. The fibers are said to possess a high capability of water imbibition. The fibers can be formed into woven fabrics, like toweling, and non-woven fabrics and wadding, such as diapers, sanitary napkins, tampons and swabs. European Patent Application 0 301 874 published Feb. 1, 1989, is directed to cellulosic fibers having a decitex of less than 5.0 and a multi-limbed cross section. The limbs have a length-to-width aspect ratio of at least 2:1. The fibers can be formed into woven, nonwoven, or knitted fabrics and are described as being especially useful for absorbent products. Japanese Kokoku Patent No. SHO 62[1987]-53605 published Nov. 11, 1987, is directed to synthetic fibers having shaped cross sectional views meeting certain criteria. Again, the fibers are said to have excellent water absorptivity when formed into nonwoven products.

When nonwoven webs containing shaped fibers are employed in disposable absorbent products, the ability to absorb a liquid is generally not sufficient to ensure optimum performance. For example, during use, many disposable absorbent products are exposed to multiple insults of a liquid. In order to ensure proper absorption of subsequent insults, it is generally desired that the first insult of liquid not only be absorbed but also transported within the absorbent products to areas remote from the point of insult. European Patent Application 0 391 814 published Oct. 10, 1990, describes the use of shaped fibers in absorbent products to transport liquids. The shaped fibers are described as possessing a specific surface area relative to diameter.

When nonwoven webs containing shaped fibers are employed in disposable absorbent products, it is desirable that the web not only be able to transport a liquid but also be able to quickly accept a liquid. Additionally, it is often desirable to be able to control the direction in which liquid present in the product is transported. This is particularly true when the width of the absorbent product is relatively narrow compared to its length. The ability to control the direction of liquid transport allows prevention of liquid transferring out the side edges of a product.

Absorbent products, which are capable of good liquid transport, are not without disadvantages. Liquids to be absorbed by such absorbent products are often applied to the products in a relatively localized area. When the liquid is subsequently transported throughout the product, a larger surface of the product tends to become wet and discolored by the absorbed liquid. This may be both uncomfortable and unattractive.

SUMMARY OF THE INVENTION

It is desirable to provide a structure for absorbing and transporting a liquid, against a pressure, to points remote from the point of liquid application, which structure is also able to mask the area of greatest liquid transport from a user.

These and other related goals are achieved in a structure comprising an upper nonwoven masking layer and a lower nonwoven distribution layer. The masking layer comprises from 0 to about 90 weight percent, based on total masking layer weight, of a shaped fiber, and from 100 to about 10 weight percent, based on total masking layer weight, of a non-shaped fiber. The distribution layer comprises from 100 to about 10 weight percent, based on total distribution layer weight, of a shaped fiber, and from 0 to about 90 weight percent, based on total distribution layer weight, of a nonshaped fiber. The distribution layer comprises at least about 10 weight percent more shaped fibers than the masking layer.

DETAILED DESCRIPTION OF THE PREFERRED EMBODIMENTS

The present invention relates to a structure for absorbing and transporting a liquid. The structure is further capable of masking, from a user, the area in which the greatest liquid transport occurs.

Figure 1:
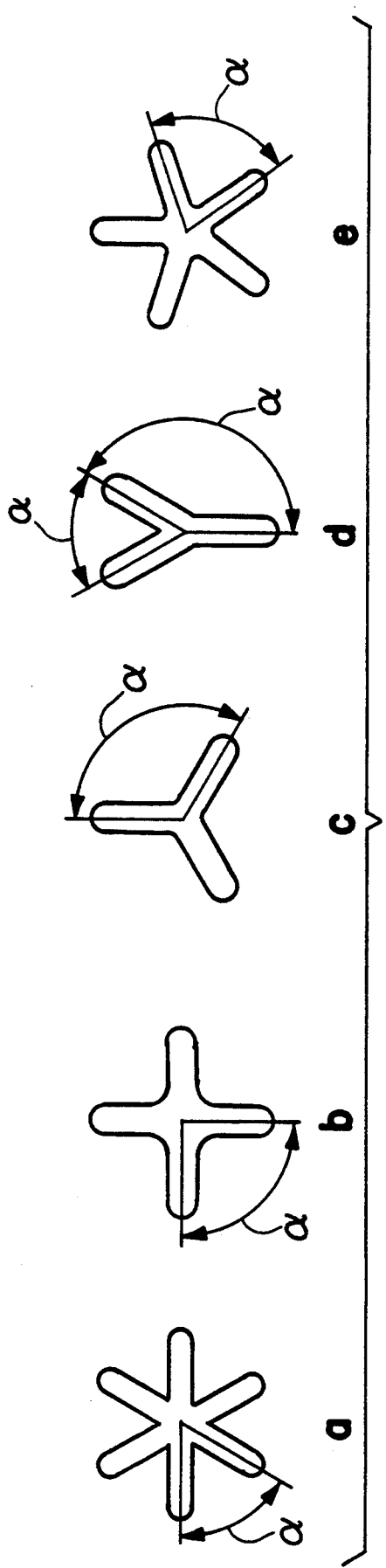
FIG. 1 is a cross-sectional illustration of shaped fibers according to the present invention.

As used herein, reference to a shaped fiber refers to a fiber which defines a notch, which notch defines an angle alpha such that:

$$\alpha < 180° - 2\theta$$

wherein $\theta$ is the contact angle between a liquid to be transported and the shaped fiber. With reference to FIG. 1, a variety of cross-sectional views of shaped fibers believed suitable for use in the present invention are illustrated. As can be seen from reference to FIG. 1a–e, the illustrated shaped fibers all define one or more angles alpha. The angles alpha defined by one individual fiber may be the same, as in FIG. 1b, or may be different, as in FIG. 1d. As used herein, reference to a nonshaped fiber refers to any fiber not falling within the definition of shaped fiber as set forth above.

Nonwoven webs formed from shaped fibers are capable of both intrafiber liquid transport and interfiber liquid transport. As used herein, reference to interfiber liquid transport refers to the situation wherein a liquid moves through a nonwoven web of fibers as a result of capillaries formed by said fibers. Those skilled in the art will recognize the vertical distance of interfiber liquid transport depends on the capillary pressure of the system. The capillary pressure of a cylindrical capillary is expressed by the equation:

$$P_c = \frac{2\gamma \cos \theta}{r}$$

wherein $P_c$ is the capillary pressure, $\gamma$ is the surface tension of the liquid, $\theta$ is the liquid-fiber contact angle, and $r$ is the capillary radius. With a given liquid, the capillary pressure (capillary force) increases with the cosine of the liquid-fiber contact angle and decreases with a larger capillary radii, such that smaller capillaries will transport a liquid farther vertically through the interfiber capillaries or against a pressure. As used herein, intrafiber liquid transport refers to the situation wherein the liquid is transported (wicked) against a pressure along the length of an individual fiber as a result of a notch or channel defined by the surface of the individual fiber. Exemplary of pressures against which the liquid may be transported are gravity, capillary pressure differentials, and the like.

As used herein, reference to the contact angle of the liquid to be absorbed and transported, and the material from which a fiber is formed, is determined as set forth by Good and Stromberg in "Surface and Colloid Science" Volume II (Plenum Press, 1979). The angle alpha, defined by the notch present in the shaped fiber, is suitably measured by scanning microscopy, optical microscopy, or other methods known to those skilled in the art.

Figure 2:
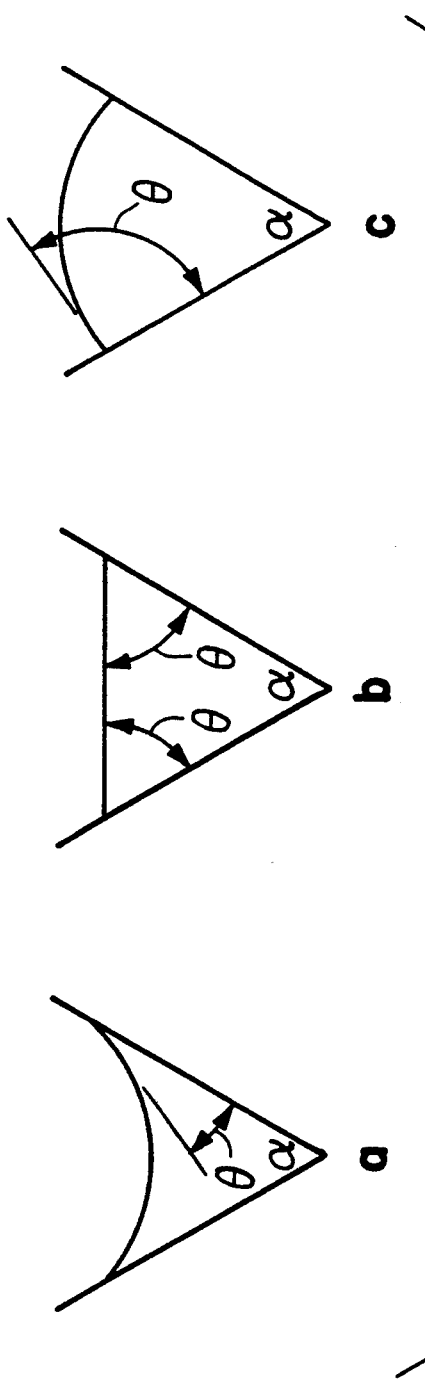
FIG. 2 represents various contact angles between shaped fibers and a liquid present in the shaped fibers.

The conditions for intrafiber liquid transport are explained in greater detail in connection with FIG. 2. In FIG. 2a–c, an enlarged notch is shown. The notches (2a–c) all define the same angle alpha. Each of the notches 2a–c is shown containing a liquid having a different liquid/fiber contact angle, in air, of $\theta$. In FIG. 2a, the liquid meniscus in the notch appears concave outward and illustrates the situation wherein $\alpha < 180° - 2\theta$. In FIG. 2b, the liquid meniscus forms a straight line in the notch and illustrates the situation wherein $\alpha = 180° - 2\theta$. In FIG. 2c, the liquid meniscus appears convex outward and illustrates the situation wherein $\alpha > 180° - 2\theta$.

Intrafiber liquid transport (wicking) occurs in the situation illustrated in FIG. 2a and does not occur in the situations illustrated in FIGS. 2b or c. The ability of a notch, defined by a fiber, to provide intrafiber wicking can be controlled by either changing the contact angle $\theta$ of the liquid to be transported or by changing the angle alpha defined by the notch.

The structures according to the present invention comprise a nonwoven masking layer and a nonwoven distribution layer. The nonwoven masking layer is superposed on the distribution layer and is in fluid communication therewith. That is, a fluid applied to the masking layer can move into and be transported by the distribution layer. The masking layer and distribution layer may be in direct contact or may have one or more layers separating the layers. The masking layer and distribution layer may be formed as separate layers or may be formed as a single structure. When the masking layer and distribution layer are formed as a single structure, the structure will have one surface having the characteristics specified for the masking layer, with the opposite surface having the characteristics specified for the distribution layer.

The masking layer comprises from 0 to about 90 weight percent, beneficially from 0 to about 75 weight percent, preferably from 0 to about 50 weight percent, and more preferably from 0 to about 25 weight percent, based on total masking layer weight, of a shaped fiber. The masking layer further comprises from 100 to about 10 weight percent, beneficially from 100 to about 25 weight percent, preferably from 100 to about 50 weight percent, and most preferably from about 100 to about 75 weight percent, based on total masking layer weight, of a nonshaped fiber.

The distribution layer comprises from 100 to about 10 weight percent, beneficially from 100 to about 25 weight percent, preferably from about 100 to 50 weight percent, more preferably from 100 to about 75 weight percent, and most preferably 100 weight percent, based on total distribution layer weight, of a shaped fiber. The distribution layer further comprises from 0 to about 90 weight percent, beneficially from 0 to about 75 weight percent, preferably from 0 to about 50 weight percent, more preferably from 0 to 25 weight percent, and most preferably 0 weight percent, based on total distribution layer weight, of a nonshaped fiber. The distribution layer comprises at least about 10 weight percent, beneficially at least about 25 weight percent, preferably at least about 50 weight percent, more preferably about 75 weight percent, and most preferably about 100 weight percent more shaped fibers than the masking layer.

Applicants have discovered that a structure comprising a masking layer and a distribution layer, wherein the distribution layer comprises at least about 10 weight percent, desirably at least about 25 weight percent, preferably at least about 50 weight percent, more preferably at least about 75 weight percent, and most preferably at least about 100 weight percent more shaped fibers than the masking layer, is capable of absorbing a liquid, transporting the liquid, and masking the area of liquid transport from a user.

As used herein, the structure comprising a masking layer and a distribution layer will be considered able to mask the area of liquid transport from a user when the distribution layer has a larger liquid transport area (interfiber and intrafiber) than the masking layer. Without intending to be bound by a theory, it is hypothesized that, due to the ability of the shaped fibers to transport a liquid through both inter and intrafiber liquid transport, a liquid will be preferentially transported by the distribution layer due to the presence of more shaped fibers.

Figure 3:
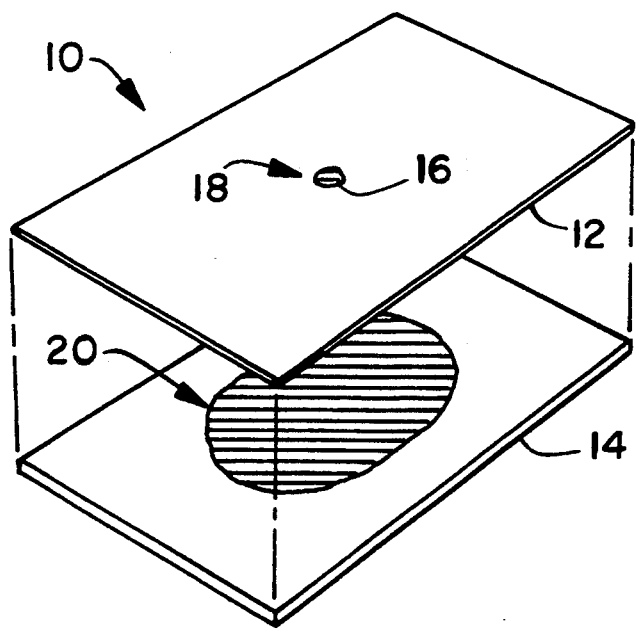
FIG. 3 illustrates an exploded view of a structure according to the present invention.

FIG. 3 illustrates an exploded view of a structure 10 according to the present invention. The structure comprises an upper masking layer 12 and a lower distribution layer 14. The masking layer 12 comprises 100 weight percent nonshaped fibers. As can be seen from reference to FIG. 3, when a liquid 16 is applied to a point on the upper surface of masking layer 12, the liquid is subjected only to interfiber liquid transport. That is, the liquid 16 is transported in the capillaries defined by the fibers forming the masking layer to form an area of interfiber liquid transport 18. The size of the interfiber liquid transport area 18 will depend on the amount of liquid applied and the capillary pressure of the system; which is, as discussed above, dependent on capillary radius, surface tension of the liquid 16, and contact angle e between the fibers and the liquid 16.

The distribution layer 14 comprises 100 weight percent of shaped fibers. As can be seen from reference to FIG. 3, the presence of shaped fibers in the distribution layer 14 allows the liquid 16 to be subjected to both interfiber and intrafiber liquid transport. Thus, the distribution layer forms an area 20 of liquid transport. The size of the area of liquid transport 20 is dependent on the amount of liquid applied and on the capillary pressure of the system. As can be seen from reference to FIG. 3, the area of liquid transport 18 remains relatively small, while the area of liquid transport 20 is considerably larger. This is due to the presence of the shaped fibers in the distribution layer, assuming the masking layer and distribution layer are otherwise the same.

In use, structure 10 would be found to be capable of transporting a liquid in the distribution layer away from a point of application. The masking layer 12 would not serve to accomplish as much liquid transport as the distribution layer but effectively masks the large area 20 of liquid transport present in the distribution layer 14. Thus, from the perspective of a user, structure 10 appears relatively unused and more attractive than if the large area of liquid transport 20 were visible to a user. Moreover, the masking layer will maintain a relatively dry feel due to the presence of the small area of liquid transport 18.

Applicants have discovered that it is possible to further control the transport of a liquid in the distribution layer by controlling the orientation of the shaped fibers in the distribution layer. That is, Applicants have found that a liquid transported in the distribution layer tends to be transported more readily in the direction in which a majority of the shaped fibers are oriented.

Figure 4:
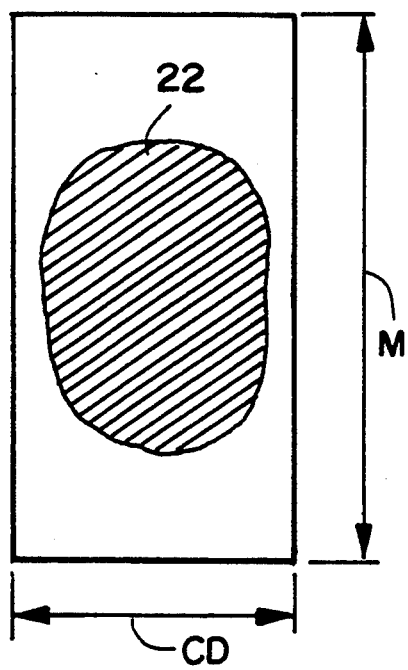
FIG. 4 illustrates a distribution layer according to the present invention.

With reference to FIG. 4, a distribution layer comprising 100 weight percent shaped fibers is illustrated. The shaped fibers have a machine direction: cross direction orientation of 1:1 as determined by tensile strength measurements. That is, as many fibers are oriented in the machine direction (MD) as in the cross direction (CD). A liquid applied to the distribution layer illustrated in FIG. 4 forms a generally circular area of liquid transport 22.

Figure 5:
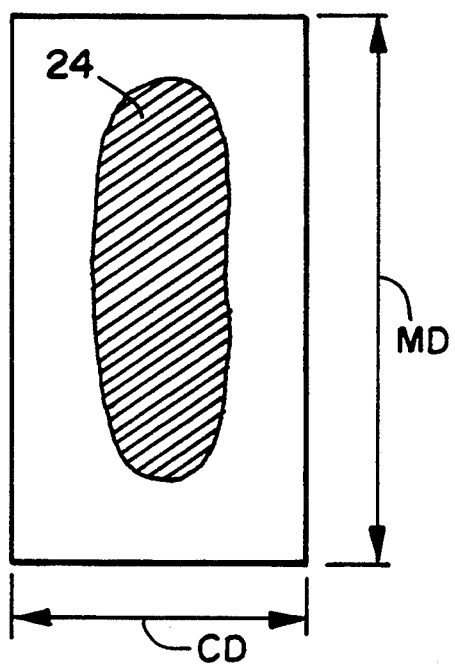
FIG. 5 illustrates a distribution layer according to the present invention.

FIG. 5 illustrates a distribution layer formed from 100 percent shaped fibers. However, unlike FIG. 4, the fibers of the distribution layer illustrated in FIG. 5 have a machine direction (MD): cross direction (CD) fiber orientation of 4:1. That is, four times as many fibers are oriented in the machine direction as in the cross direction. A liquid applied to the distribution layer illustrated in FIG. 5 forms an elliptical area 24 of liquid transport. For the purpose of this application, fiber orientation will be assumed to be directly related to tensile strength. Thus, a web having a machine direction: cross direction tensile strength ratio of 2:1 will be assumed to have a machine direction: cross direction fiber orientation of 2:1.

Applicants have found that the ability to control the area of liquid transport through shaped fiber orientation is particularly useful when the structures, according to the present invention, are employed as the absorbent cores in feminine napkins. Those skilled in the art will recognize that feminine napkins are generally relatively narrow in order to fit comfortably between the legs of a wearer. The feminine napkins may be relatively long compared to their width. Due to the relatively narrow nature of feminine napkins, it is not unusual for feminine napkins to leak out of the side edges when the absorbent becomes saturated in the central section while portions of the napkin near the longitudinal ends remain unused. Accordingly, it would be desirable to be able to cause liquid absorbed by a feminine napkin to be transported, preferentially, in the longitudinal direction as opposed to the transverse direction. Use of a distribution layer, having the shaped fibers present therein oriented preferentially in a longitudinal (machine) direction, is one way of accomplishing this preferential liquid transport.

In order to allow the masking layer to perform a masking function, it is desirable that the majority of the liquid transport occur in the distribution layer. As discussed above, the presence of more shaped fibers in the distribution layer is one manner of accomplishing this. The preferential liquid transport by the distribution layer, as opposed to the masking layer, can be enhanced by forming the masking layer and distribution layer such that the masking layer has a lower density than the distribution layer and/or is formed from fibers having a larger average diameter.

In a preferred embodiment of the present invention, the liquid transport in a multi-layered structure can be highly controlled and optimized by carefully selecting the four variables discussed above. Specifically, fiber shape, fiber orientation, density and fiber diameter of the layers can be selected to produce the desired liquid transport properties. The higher the concentration of shaped fibers, the more distribution obtained in a given layer. Similarly, higher density and smaller average fiber diameter allows a layer to perform more liquid transport. Fiber orientation allows for control of the liquid transport pattern.

For example, if it is desired to maximize the difference in liquid distribution properties between the two layers, the masking layer would be formed from non-shaped fibers having a relatively large average diameter and would have a relatively low density and a relatively low degree of fiber orientation. The distribution layer would be formed from shaped fibers having a relatively small average diameter and would have a relatively high density and a relatively high degree of fiber orientation compared to the masking layer.

Similarly, a given, less than maximized, difference in the liquid transport properties between the two layers can be achieved in a number of ways. For example, the two layers could be identical with respect to fiber diameter, fiber orientation and density, but differ in that the masking layer contains no shaped fibers, while the distribution layer contains 75 weight percent of shaped fibers. The masking layer and distribution layer will have different liquid transport properties. An equivalent difference may be obtained when the masking layer contains no shaped fibers and the distribution layer contains only 50 weight percent shaped fibers by either increasing the density of the distribution layer, decreasing the average fiber diameter of the distribution layer or a combination of the two. The relationship between fiber shape, fiber diameter, density and fiber orientation in a multi-layered composite has not heretofore been recognized.

As a general rule, the masking layer and the distribution layer will have a density within the range of from about 0.03 to about 0.3, preferably of from about 0.05 to about 0.17 grams per cubic centimeter. When it is desired to enhance the preferential liquid transport by the distribution layer, the distribution layer suitably has a density at least about 10 percent, preferably at least about 50 percent, and most preferably at least about 100 percent greater than the masking layer.

The fiber orientation of the fibers in the masking layer and the distribution layer will generally be from about 1:1 to about 25:1. In one preferred embodiment, the masking layer has a fiber orientation of from about 1:1 to about 2:1 and the distribution layer has a fiber orientation of from about 1:1 to about 12:1 with the distribution layer having a greater fiber orientation than the masking layer.

The shaped fibers can be formed from any material capable of forming a nonwoven web and defining a notch defining an angle, as described above, in connection with the shaped fibers. As a general rule, the shaped fibers are formed from a cellulose derivative, such as rayon or cellulose acetate, or from a synthetic polymeric material, such as polyolefins, polyesters, polyamides, polyurethanes, and the like. The materials from which the shaped fiber can be formed may be either hydrophilic or hydrophobic.

As used herein, "hydrophilic" refers to fibers having a water-in-air contact angle of less than 90° as determined as set forth by Good and Stromberg in "Surface and Colloid Science" Volume II, (Plenum Press, 1979). "Hydrophobic" refers to fibers having a water-in-air contact angle greater than 90° as set forth by Good and Stromberg in "Surface and Colloid Science" Volume II, (Plenum Press, 1979). When the shaped fibers are formed from hydrophobic material, the fibers must be treated to provide them with a hydrophilic surface. This is necessary, since hydrophobic fibers cannot meet the requirement that $\alpha < 180° - 2\theta$ if $\theta$ is greater than 90°. Methods of providing hydrophobic materials with a hydrophilic surface are known. Exemplary of such a method is the application of the surfactant or other hydrophilizing agent to the fibers. Similarly, if a hydrophilic polymer having a contact angle of less than 90° is desired to be rendered more hydrophilic to thereby decrease its contact angle, with respect to a given liquid, it is possible to treat the hydrophilic material with a surfactant or other hydrophilizing agent to impart a more hydrophilic surface. The hydrophilizing treatment may be either fugitive or nonfugitive with respect to the shaped fiber.

Methods of forming shaped fibers are known to those skilled in the art. As a general rule, shaped fibers formed from a synthetic polymeric material are generally prepared by extruding the fibers through a die orifice generally corresponding to the desired shape. Such a method is described in U.S. Pat. No. 2,945,739 issued Jul. 19, 1960, to Lehmicke, or in Japanese Kokoku Patent No. SHO 62[1987]-53605. If the shaped fiber is to be formed from a cellulosic derivative such as rayon, the shaped fiber can be formed from conventional viscose and is conveniently spun from standard viscose compositions using the standard viscose spinning conditions; with the exception that shaped extrusion holes in the spinneret are substituted for the conventional circular shaped holes. Such a method is described in European Patent Application 0 301 874 published Feb. 1, 1989. Alternatively, the shaped fiber may be formed from cellulose acetate. For example, Y-shaped cellulose acetate fibers, commercially available from Hoechst-Celanese Corporation, Narrows, Va., under the trade designation CELLULOSE ACETATE TOW and trilobal rayon, commercially available from Courtaulds Fibers, Inc. Cornwall, Ontario, Canada, under the trade designation Galaxy TM, have been found suitable for use in the present invention. Further, the shaped fiber may be formed by twisting two fibers together. The twisting of the two fibers forms a helical notch which may be capable of intrafiber liquid transport.

The shaped fibers according to the present invention generally have an average diameter of from about 0.25 micrometer to about 500 micrometers, preferably of from about 0.5 micrometer to about 40 micrometers.

The shaped fibers employed in the nonwoven webs according to the present invention define at least one notch, which notch defines an angle alpha as described above. As can be seen from reference to FIG. 1, shaped fibers, suitable for use in the present, invention may have a variety of cross-sectional shapes and often define more than one notch. The fibers may define two, three, or more notches. Each notch may have generally the same angle alpha or may define notches having several different angles. As a general rule, it is preferred that the shaped fibers employed in forming the nonwoven webs of the present invention define two, preferably three, and most preferably at least four notches, which notches define an angle alpha as described above.

Nonshaped fibers, suitable for use in the present invention, may be formed from the same materials as the shaped fibers. That is, the non-shaped fibers may be formed from cellulose derivatives or from synthetic polymeric resins. Exemplary of suitable nonshaped fibers, for use in the present invention, are generally circular rayon fibers or generally circular cellulose acetate fibers. Methods of forming such nonshaped fibers are known to those skilled in the art. The nonshaped fibers suitably have average fiber diameters as set forth above in connection with the shaped fibers.

Nonwoven webs, according to the present invention, can suitably be formed in any manner capable of forming nonwoven webs known to those skilled in the art. For example, the nonwoven webs may be formed through a carding process, rando process, spunbond process, needle punch process, and the like. Additionally, while the structures according to the present invention have been generally described in terms of a masking layer and a distribution layer, it is to be understood that the structures need not comprise two separately formed layers. The layers may be formed in generally the same process, one on top of another, while actually maintaining their individual character.

Further, it is anticipated that the masking layer and distribution layer could be formed in a single integrated structure, such that the concentration of shaped fibers decreases from one planar surface of the structure to the other, opposed, planar surface of the structure. That is, a structure having first and second planar surfaces could be formed such that the first planar surface comprises more shaped fibers than the second planar surface. In such a structure, it is anticipated the fiber orientation between the first and second planar surfaces may be the same, however, the fiber orientation may be varied between the planar surfaces, as may the density and average fiber diameter.

The structures, according to the present invention, can have a wide variety of basis weights. Suitably the structures have a basis weight of from about 15 to about 500, preferably of from about 30 to about 150 grams per square meter. When the structures comprise a separate masking layer and distribution layer, the masking layer may suitably have a basis weight of from about 5 to about 250, preferably of from about 15 to about 30 grams per square meter, and the distribution layer suitably has a basis weight of from about 5 to about 400, and preferably of from about 35 to about 100 grams per square meter. In one preferred embodiment, the distribution layer has a basis weight which is at least about 65 percent, and preferably at least about 100 percent greater than the masking layer.

The structures according to the present invention may comprise a high-absorbency material. The high absorbency material may be present in either the masking layer or the distribution or both. However, it is anticipated that the greatest benefit may be achieved by having the high-absorbency material located in the distribution layer. Specifically, it is believed that the greatest benefit may be achieved by having the high-absorbency material located in an area of intrafiber liquid transport. When the high-absorbency material is in liquid communication with one of the nonwoven webs in an area of intrafiber liquid transport, the high-absorbency material may contact the liquid transported by the notches in the shaped fibers. When the high-absorbency material is in contact with the liquid in an area of intrafiber liquid transport, the high-absorbency material is able to absorb the liquid, thus improving utilization of the high-absorbency material and allowing continued intrafiber liquid transport. When a high-absorbency material, capable of, for example, absorbing twenty times its weight in a liquid, is in contact with a liquid in an area of intrafiber liquid transport, the shaped fiber will continue to transport liquid to the high-absorbency material until the absorption capacity of the high-absorbency material is reached or until there is no more available liquid for the shaped fiber to transport.

Intrafiber liquid transport allows for improved utilization of high-absorbency material present in, or in liquid communication with, the nonwoven webs. That is, it is possible to disperse a given amount of high-absorbency material in a nonwoven web (or in liquid communication with a nonwoven web) over a greater area when intrafiber liquid transport occurs than when intrafiber liquid transport does not occur.

High-absorbency materials suitable for use in the present invention include both inorganic and organic high-absorbency materials. Suitable inorganic high-absorbency materials include, for example, absorbent clays and silica gels. Organic high-absorbency materials can include natural materials, such as agar, pectin, guar gum, and peat moss, as well as synthetic materials, such as synthetic hydrogel polymers. Such hydrogel polymers include, for example, carboxymethylcellulose, alkali metal salts of polyacrylic acid, polyacrylamides, polyvinyl alcohol, ethylene maleic anhydride copolymers, polyvinyl ethers, hydroxypropylcellulose, polyvinyl morpholinone, polymers and copolymers of vinyl sulfonic acid, polyacrylates, polyacylamides, polyvinyl pyrridine, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water-insoluble. Cross-linking may, for example, be by irradiation or by covalent, ionic, Van der Waals, or hydrogen bonding. Suitable high-absorbency materials are available from various commercial vendors such as the Dow Chemical Company, Celanese Corporation, Allied-Colloid, and Stockhausen. Typically, the high-absorbency material is capable of absorbing at least about 15 times its weight in water and preferably is capable of absorbing at least about 25-30 times its weight in water. The high-absorbency material can be present in the nonwoven web in an amount of from about 1 to about 95 weight percent, and preferably of from about 40 to about 90 weight percent, based on total weight of the nonwoven web.

Figure 6:
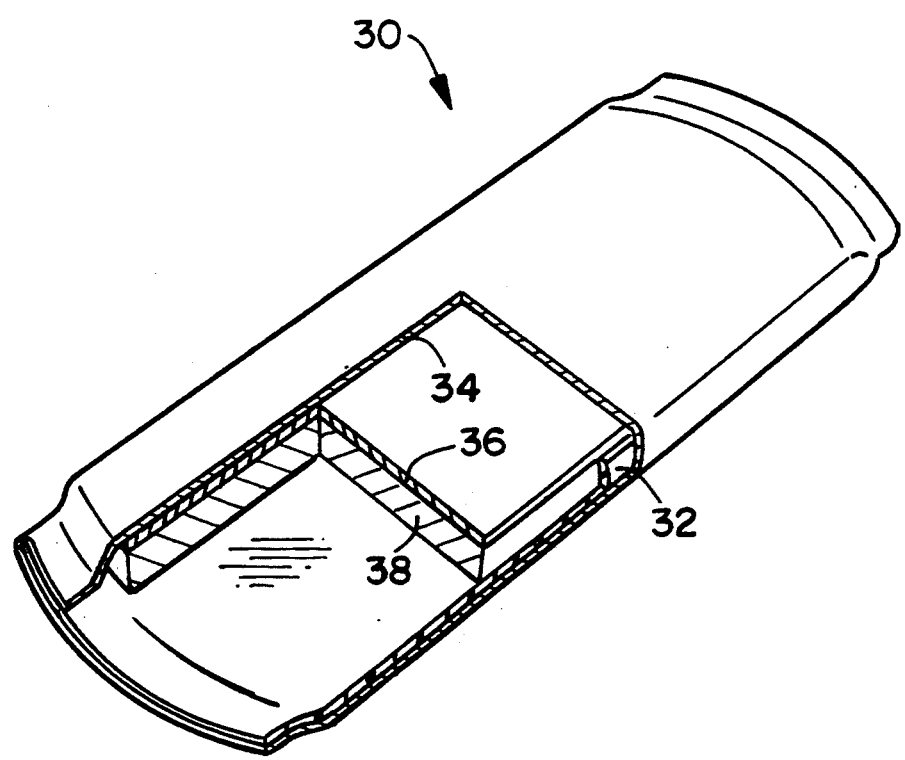

The structures according to the present invention are suitable for use in a variety of disposable absorbent products. For example, the nonwoven webs are suitable for use in personal care products such as diapers, adult incontinence products, feminine care products, training pants, wound dressings and the like. With reference to FIG. 6, a suitable absorbent personal care product is a feminine napkin 30 which comprises a fluid-impervious baffle 32, fluid-pervious outer cover 34, adapted to contact the skin of a wearer and surrounding the napkin 30, and an absorbent structure according to the present invention located between the outer cover and baffle. The absorbent structure comprises a masking layer 36 and a distribution layer 38. Exemplary of personal care products in which the structures of the present invention may be employed are those described in U.S. Pat. Nos. 4,944,735 issued Jul. 31, 1990 to Mokry; 4,798,603 issued Jan. 17, 1989, to Meyer et al.; 4,710,187 issued Dec. 1, 1987, to Boland et al.; 4,770,656 issued Sep. 13, 1988, to Proxmire et al.; and 4,762,521 issued Aug. 9, 1988, to Roessler et al.

EXAMPLES

The following webs are formed:

A. A web having a basis weight of about 34 grams per square meter is formed from 8 denier rayon fibers having a length of about 3 inches and a generally circular cross section. The fibers have a 0.14 weight percent based on total fiber weight, Leomin TM surface finish. The fibers are commercially available from Courtaulds Fibers Inc. The web is formed on a machine for airlaying staple fibers, known as a Rando-Webber machine, commercially available from the Rando Corporation, New York. The web has a generally random fiber orientation; that is, a machine direction:cross direction fiber orientation of about 1:1 as determined by tensile strength measurements. The web has a density of about 0.05 grams per cubic centimeter.

B. A web having a basis weight of about 34 grams per square meter is formed from 85 weight percent of a 3 denier rayon fiber having a length of about 1.5 inches and a generally circular cross section and 15 weight percent of a polyethylene/polyester sheath/core binder fiber. The rayon fibers have a 0.13 weight percent, based on total fiber weight, glycerol surface finish and are commercially available from Courtaulds Fibers Inc. The binder fiber is commercially available from Hoechst-Celanese Corporation under the trade designation K-54. The web is formed on a machine for airlaying staple fibers, known as a Rando-Webber machine, commercially available from the Rando Corporation, New York. The machine produces a web having a generally random fiber orientation; that is, a machine direction:- cross direction fiber orientation of about 1:1 as determined by tensile strength measurements. The web has a density of about 0.05 grams per cubic centimeter.

C. A web having a basis weight of about 34 grams per square meter is formed from 85 weight percent of a 3 denier rayon fiber having a length of about 1.5 inches and a generally trilobal cross section and 15 weight percent of a polyethylene/polyester sheath/core binder fiber. The rayon fibers have a 0.13 weight percent, based on total fiber weight, glycerol surface finish and are commercially available from Courtaulds Fibers Inc. under the trade designation Galaxy TM. The trilobal cross section is generally similar to that illustrated in FIGS. 1c and 1d. The trilobal rayon constitutes a shaped fiber, according to the present invention, when the liquid to be transported is water. The binder fiber is commercially available from Hoechst-Celanese Corporation under the trade designation K-54. The web is formed on a machine for airlaying staple fibers, known as a Rando-Webber machine, available from the Rando Corporation, New York. The machine forms a web having a generally random fiber orientation; that is, the web has a machine direction:cross direction fiber orientation of about 1:1 as determined by tensile strength measurements. The web has a density of about 0.05 grams per cubic centimeter.

D. A nonwoven web having a basis weight of 34 grams per square meter is prepared from the rayon and binder fibers (85/15) used to make web C as described above. This web is identical to web C with the exception that the web is formed by carding the fibers such that the web has a machine direction:cross direction fiber orientation of about 6:1 as determined by tensile strength measurements. The web ha a density of about 0.05 grams per cubic centimeter.

The webs described above are employed to form absorbent structures according to the present invention and comparative examples.

The absorbent structures formed from the webs are then tested to determine fluid distribution properties. The test method involves providing a 10 inch by 6 inch test sample. The test sample is placed on a nylon mesh screen having ⅛ inch openings. The screen is suspended in air. To the upper surface of the absorbent structure is applied 20 drops of colored water. The water is applied to the center of the test sample. The length and width of the stain size on the bottom surface of the test sample (the surface opposite the surface of water application) is measured after reaching equilibrium (about 20 minutes).

Table 1 sets forth the exact configuration of the absorbent structures prepared and the stain sizes (bottom surface) determined as set forth above. All of the tested samples have stains on the upper surface, which stains are generally circular, and have a diameter of about 1½ to 2 centimeters. Samples numbers 3, 4, 6, 7, and 8 possess density gradients. The density gradients are introduced into the absorbent structures by forming the absorbent structure and compressing it in a Carver press with the top plate heated to approximately 110°–120° C. For sample numbers 3, 4, 6, and 8, the surface adjacent the heated (top) plate becomes densified. For sample number 7, the surface opposite the heated (top) plate becomes densified.

TABLE 1

| Sample No. | Configuration[1] | Cross-Section | Density (g/cc) | Orientation (MD:CD) | Stain (bottom) length (cm) width (cm) |
|---|---|---|---|---|---|
| 1* | A | Circular | 0.05 | 1:1 | 3.1/2.9 |
|  | B | Circular | 0.05 | 1:1 |  |
|  | B | Circular | 0.05 | 1:1 |  |
| 2 | A | Circular | 0.05 | 1:1 | 7.8/7.5 |
|  | C | Trilobal | 0.05 | 1:1 |  |
|  | C | Trilobal | 0.05 | 1:1 |  |
| 3 | A | Circular | 0.05 | 1:1 | 8.5/7.5 |
|  | C | Trilobal | 0.09 | 1:1 |  |
|  | C | Trilobal | 0.17 | 1:1 |  |
| 4 | A | Circular | 0.05 | 1:1 | 12.2/8.3 |
|  | D | Trilobal | 0.09 | 6:1 |  |
|  | D | Trilobal | 0.17 | 6:1 |  |
| 5 | A | Circular | 0.05 | 1:1 | 7.3/4.5 |
|  | D | Trilobal | 0.05 | 6:1 |  |
|  | D | Trilobal | 0.05 | 6:1 |  |
| 6 | A | Circular | 0.05 | 1:1 | 12.2/8.3 |
|  | D | Trilobal | 0.09 | 6:1 |  |
|  | D | Trilobal | 0.17 | 6:1 |  |
| 7* | A | Circular | 0.05 | 1:1 | 6.9/4.4 |
|  | A | Circular | 0.09 | 1:1 |  |
|  | A | Circular | 0.17 | 1:1 |  |
| 8* | A | Circular | 0.05 | 1:1 | 8.5/8.0 |
|  | B | Circular | 0.09 | 1:1 |  |
|  | B | Circular | 0.17 | 1:1 |  |

*Not an example of the present invention
[1]Configuration of described webs forming absorbent structure. The upper web forms the upper surface. Thus for Sample 2, web A is the masking layer, with the two web C's acting as distribution layers.

As can be seen from comparison of sample numbers 1 and 2, the presence of the trilobal fibers in sample number 2 greatly influences the stain size when compared to sample number 1. Sample numbers 1 and 2 are otherwise identical.

From comparison of sample numbers 2 and 3, it is seen that web 3 possesses a density gradient whereby the masking layer A has a lower density than the distribution layers C. Sample 3 is seen to have a larger stain size than sample 2.

As can be seen from reference to sample numbers 3 and 4, providing web 4 with a machine direction:cross direction fiber orientation of 6:1 produces a larger stain size than that of sample 3.

As can be seen from comparison of sample numbers 5 and 6, the presence of a density gradient in sample 6, such that the masking layer has a relatively low density compared to the distribution layers in combination with a high degree of fiber orientation in the distribution layer, produces a stain having a greater size than in the identical structure (sample 5) wherein the density gradient does not exist.

Finally, as can be seen from comparison of sample numbers 7 and 8, forming the lower layers with fibers having a smaller average fiber diameter also influences the size of the stain. Specifically, a larger stain is produced. While sample number 8 does not possess shaped fibers as required by the present invention, it was desirable to employ generally circular cross sectional fibers to isolate the effect of fiber size. The same general effect is seen when the shaped fibers of the distribution layer of the present invention have a generally smaller fiber diameter than the fibers of the masking layer.

From the above, it is seen that the structures according to the present invention are capable of performing a masking and distribution function. Additionally, it is seen that this ability is enhanced by further providing a density gradient, a difference in fiber orientation, and/or a difference in fiber size.

While the above invention has been described in specific terms and illustrated in specific embodiments, those skilled in the art will appreciate that the specific examples and embodiments set forth above are capable of numerous modifications and variations, which modifications and variations are nonetheless within the scope of the invention. Accordingly, the specific embodiments discussed above and the specific examples set forth above are not intended to limit, in any manner, the scope of the invention as set forth in the appended claims.

What is claimed is:

1. A structure for absorbing and transporting a liquid, said structure comprising:
   a) a nonwoven masking layer, said masking layer comprising;
      1) from greater than 0 to about 90 weight percent, based on total masking layer weight, of a shaped fiber, said shaped fiber defining a notch, said notch defining an angle alpha such that $alpha < 180° - 2\theta$ wherein $\theta$ is the contact angle between a liquid and said shaped fibers; and
      2) from less than 100 to about 10 weight percent, based on total masking layer weight, of a nonshaped fiber; and
   b) a nonwoven distribution layer, said distribution layer comprising:
      1) from 100 to about 10 weight percent, based on total distribution layer weight of a shaped fiber, said shaped fiber defining a notch, said notch defining an angle alpha such that $alpha < 180° - 2\theta$ wherein $\theta$ is the contact angle between a liquid and said shaped fibers; and
      2) from 0 to about 90 weight percent, based on total distribution layer weight, of a nonshaped fiber; wherein said distribution layer comprises at least about 10 weight percent more shaped fibers than said masking layer.

2. A structure according to claim 1 wherein said masking layer comprises from greater than 0 to about 75 weight percent shaped fibers and said distribution layer comprises from about 25 to 100 weight percent shaped fibers.

3. A structure according to claim 2 wherein said masking layer comprises from greater than 0 to about 50 weight percent shaped fibers and said distribution layer comprises from about 50 to 100 weight percent shaped fibers.

4. A structure according to claim 3 wherein said masking layer comprises from greater than 0 to about 25 weight percent shaped fibers and said distribution layer comprises from about 50 to 100 weight percent shaped fibers.

5. The structure according to claim 4 wherein said masking layer comprises nonshaped fibers having a generally circular cross section.

6. A structure according to claim 1 wherein said shaped fibers define three notches, each notch defining an angle alpha such that $alpha < 180° - 2\theta$, wherein $\theta$ is the contact angle between said liquid and said shaped fiber.

7. A structure according to claim 1 wherein said distribution layer comprises at least about 25 weight percent more shaped fibers than said masking layer.

8. A structure according to claim 7 wherein said distribution layer comprises at least about 50 weight percent more shaped fibers than said masking layer.

9. A structure according to claim 8 wherein said distribution layer comprises at least about 75 weight percent more shaped fibers than said masking layer.

10. A structure according to claim 1 wherein said masking layer has a fiber orientation of from about 1:1 to about 1:2, and said distribution layer has a fiber orientation of from about 1:1 to about 1:12, said distribution layer having a greater fiber orientation than said masking layer.

11. A structure according to claim 1 wherein said distribution layer has a density at least about 10 percent greater than the density of said masking layer.

12. A structure according to claim 1 wherein said distribution layer has a basis weight greater than the basis weight of said masking layer.

13. A structure according to claim 1 wherein said masking layer has a lower density, a smaller average fiber diameter and lower degree of fiber orientation than said distribution layer.

14. A structure according to claim 1 wherein said distribution layer has a higher degree of fiber orientation than said masking layer.

15. A structure for absorbing and transporting a liquid, said structure comprising shaped and nonshaped fibers and having a first planar surface, wherein said first planar surface comprises, based on total first planar surface weight, from less than 100 to about 10 weight percent of said nonshaped fibers and from greater than 0 to about 90 weight percent of said shaped fibers; and a second planar surface, said second planar surface comprising, based on total second planar surface weight, from 100 to about 10 weight percent of said shaped fibers and from 0 to about 90 weight percent of a nonshaped fiber wherein said second planar surface comprises at least about 10 weight percent more shaped fibers than said first planar surface, wherein said shaped fibers define a notch, said notch defining an angle alpha such that $$\text{alpha} < 180° - 2\theta$$

wherein $\theta$ is the contact angle between a liquid and said shaped fibers.

16. A structure according to claim 15 wherein said second planar surface comprises from 25 to 100 weight percent shaped fibers.

17. A structure according to claim 16 wherein said second planar surface comprises from about 50 to 100 weight percent shaped fibers.

18. A structure according to claim 15 wherein said second planar surface comprises at least about 25 weight percent more shaped fibers than said first planar surface.

19. A structure according to claim 18 wherein said second planar surface comprises at least about 50 weight percent more shaped fibers than said first planar surface.

20. A structure according to claim 15 wherein said first planar surface has a fiber orientation of from about 1:1 to about 1:2, and said second planar surface has a fiber orientation of from about 1:1 to about 1:12.

21. A structure according to claim 15 wherein said second planar surface has a density at least about 10 percent greater than the density of said first planar surface.

22. A structure according to claim 15 wherein said second planar surface comprises fibers having a smaller average diameter than fibers comprising the first planar surface.

23. A structure according to claim 15 wherein said second planar surface comprises fibers having a smaller average diameter than fibers comprising the first planar surface.

24. The structure according to claim 1 wherein the nonshaped fiber is formed from a material selected from the group consisting of a cellulose derivative and a synthetic polymeric material.

25. The structure according to claim 24 wherein the nonshaped fiber is formed from a cellulose derivative.

26. The structure according to claim 25 wherein the nonshaped fiber is formed from a material selected from the group consisting of rayon fibers and cellulose acetate fibers.

27. The structure according to claim 24 wherein the nonshaped fiber is formed from a synthetic polymeric material.

* * * * *